(12) United States Patent
Paonessa et al.

(10) Patent No.: US 8,148,533 B2
(45) Date of Patent: Apr. 3, 2012

(54) IONIC LIQUIDS OF HETEROCYCLIC AMINES

(75) Inventors: Martin A. Paonessa, Niagara Falls, NY (US); Rajiv R Singh, Getzville, NY (US); Valentine T Zuba, Orchard Park, NY (US); George A Shia, Amherst, NY (US); John A McFarland, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 1466 days.

(21) Appl. No.: 11/072,964

(22) Filed: Mar. 4, 2005

(65) Prior Publication Data

US 2005/0196671 A1    Sep. 8, 2005

Related U.S. Application Data

(60) Provisional application No. 60/550,471, filed on Mar. 5, 2004.

(51) Int. Cl.
| | |
|---|---|
| C07D 211/00 | (2006.01) |
| C07D 211/70 | (2006.01) |
| C07D 277/08 | (2006.01) |
| C07D 263/02 | (2006.01) |
| C07D 263/30 | (2006.01) |
| C07D 233/00 | (2006.01) |
| C07D 207/00 | (2006.01) |

(52) U.S. Cl. ........ 546/184; 546/348; 548/146; 548/215; 548/235; 548/300; 548/400

(58) Field of Classification Search .... 546/1; 548/300.1
See application file for complete search history.

(56) References Cited

U.S. PATENT DOCUMENTS

| | | | | |
|---|---|---|---|---|
| 5,073,674 | A | * 12/1991 | Olah | 585/725 |
| 5,965,054 | A | 10/1999 | McEwen et al. | 252/62.2 |
| 7,145,046 | B2 | 12/2006 | Braun et al. | |
| 2004/0097758 | A1 | 5/2004 | Braun et al. | |

FOREIGN PATENT DOCUMENTS

| | | |
|---|---|---|
| EP | 1380569 | 1/2004 |
| EP | 1095934 | * 3/2004 |
| JP | 57-092502 | 6/1982 |
| JP | 72920490 | 11/1995 |
| JP | 8239787 | 9/1996 |
| JP | 2003313181 | 11/2003 |
| WO | WO00/56700 | 9/2000 |
| WO | WO02/060838 | 8/2002 |
| WO | WO03/061803 | 7/2003 |
| WO | WO2005/007657 | 1/2005 |

OTHER PUBLICATIONS

"A Highly conductive Room Temperature Molten Fluoride: EMIF-2.3HF", Hagiwara et. al., Journal of the Electrochemical Society, 149, (1) D1-D6, 2002.*

Johnson, K. Electrochem. Soc. 2007, pp. 38-42.*
Olah, G. et al. J. Am. Chem. Soc., 127, 2005, 5964-69.*
Olah, G. et al., J. Org. Chem., 44, 1979, pp. 3872-81.*
Hagiwara et al., "Acidic 1-ethyl-3-methylimidazolium flouride: a new room temperature ionic liquid," *Journal of Flourine Chemistry*, 99, 1-3(1999).
Hagiwara et al., "A Highly Conductive Room Temperature Molten Flouride: EMIF-2.3 HF," *Journal of Electrochemical Society*, 149(1), D1-D6(2002).
Welton, "Room-Temperature Ionic Liquids. Solvents for synthesis and catalysis," *Chem. Rev.*, 99, 2071-2083(1999).
Hong et al., "Conventional free radical polymerization in room temperature ionic liquids: A Green Approach to Commodity Polymers with practical Advantages," *Chem. Comm.*, 1368-1369(2002).
Scott et al., Application of ionic liquids as plasticizers for poly(methyl methacrylate), *Chem. Comm*, 1370-1371(2002).
Klilngshirn et al., "Polar, non-coordinating ionic liquids as solvents for the alternating copolymerization of styrene and CO catalyzed by cationic palladium catalysts," *Chem. Comm.*, 1394-1395(2002).
Swatloski et al. "Dissolution of cellose [(sic.)] with Ionic Liquids," *J. Am. Chem. Soc.*, 124, 4974-4975(2002).
Sheldon et al., "Biocatalysis in ionic liquids," *Green Chem.*, 4,147-151(2002).
Sheldon, "Catalytic reactions in Ionic liquids,"*Chem. Comm.*,2399-2407(2001).
Huddleston et al., "Characterization and comparison of hydrophilic and hydrophobic room temperature ionic liquids incorporating the imidazolium cation," *Green Chem.*, 3, 156-164(2001).
Holbrey et al., "Ionic Liquids (rev.)," *Clean Products and Proc.*, 1, 223-236(1999).
Gordon, "New Developments in Catalysis using ionic liquids," *Applied Catalysis A: General*, 222,101-117(2001).
Wasserscheid et al., "Ionic Liquids—New "Solutions" for Transition Metal Catalysis," *Angew. Chem. Int. Ed.*, 39, 3772-3789(2000).
JACS vol. 110 No. 7 1988 pp. 2135-2139 XP002339918.
Dagmar Boenigk et al.; "The System Pyrioine-Hydrogen Fluoride at Low Temperatures: Formation and Crystal Structures of Solid Complexes With Very Strong NHF and FHF Hydrogen Bonding"; J. Am. Chem. Soc. 1988, 110, 2135-2139.
Makoto UE, et al., "Application of Low-Viscosity Ionic Liquid to the Electrolyte of Double-Layer Capacitors": Journal of the Electrochemical Society, 2003, 15, A499-A502.

* cited by examiner

*Primary Examiner* — Janet Andres
*Assistant Examiner* — Heidi Reese
(74) *Attorney, Agent, or Firm* — DLA Piper LLP (US)

(57) ABSTRACT

Ionic liquids having melting points below about 100 C formed by reaction of a heterocyclic amine with about 2.8 and about 3.2 moles of anhydrous hydrogen fluoride per mole of amine nitrogen. Electrochemical devices having non-aqueous electrolytes containing the ionic liquids are also disclosed, as well as silicon oxide etching compositions containing the ionic liquids and etching methods in which silicon oxides are selectively removed by the etching compositions in the presence of aluminum.

13 Claims, No Drawings

IONIC LIQUIDS OF HETEROCYCLIC AMINES

CROSS REFERENCE TO RELATED APPLICATION

The present application claims priority benefit under 35 U.S.C. §119(e) of U.S. Provisional Application No. 60/550, 471 filed Mar. 5, 2004, the disclosure of which is incorporated herein by reference.

BACKGROUND OF THE INVENTION

The present invention relates to ionic liquids and methods for their preparation. In particular, the present invention relates to ionic liquids that are liquid at relatively low temperatures. Compounds according to the present invention are liquid at temperatures below about 100° C., and are preferably liquid below about 60° C., and more preferably are liquid at or near ambient temperature.

There is currently great interest in the use of ionic liquids as solvents for a wide range of applications. Ionic liquids are low melting point salts that, being composed entirely of ions, posses negligible vapor pressures. By carefully choosing among a wide range of possible cations and anions, ionic liquids may be prepared that are liquid at low temperatures. A number of other solvent properties can be controlled as well, such as polarity and other factors that determine a liquid's suitability as a solvent for a given end-use application.

Conventional organic solvents are high on the list of hazardous chemicals because they are typically volatile liquids that are used in large quantity and produce harmful vapors that are difficult to contain. Ionic liquids, on the other hand, are non-volatile, non-flammable and highly stable solvents, and as such are rapidly emerging as promising replacements for the traditional volatile organic solvents.

Not only do ionic liquids have utility as industrial solvents, they are also suitable, for example, as highly polar solvents for use in preparative chemistry, and as catalysts. The negligible vapor pressure of ionic liquids facilitates product separation by fractional distillation. They also have particular application in electrochemistry, for example, in batteries, fuel cells, photovoltaic devices and in electrodeposition processes.

International Application No. PCT/GB00/01090 discloses ionic liquids that are specific quaternary ammonium salts of zinc, tin and iron halides. The disclosed ionic liquids are reportedly liquid below 60 C and inexpensive to produce. The quaternary ammonium salts of zinc, tin and iron halides are reportedly less water sensitive that earlier prior art ionic liquids, which were quaternary ammonium salts of aluminum trichloride.

Hagiwara et al., *J. Fluorine Chem.*, 99, 1 (1999), and *J. Electrochem. Soc.*, 149, D1 (2002), recently disclosed several ionic liquids comprising various imidazolium fluorides combined with hydrogen fluoride at a specific mole ratio of 1:2.3. Otherwise, prior art salts are minimally electrically conductive, and all are viscous liquids. There remains a need for ionic liquids with greater fluidity for solvent applications and with an electrical conductivity better suited for electrochemical applications.

DETAILED DESCRIPTION OF PREFERRED EMBODIMENTS

This need is met by the present invention. It has now been discovered that ionic liquids that are formed from heterocyclic amines using approximately three moles of hydrogen fluoride per amine nitrogen are orders of magnitude more electrically conductive than the quaternary ammonium salts of zinc, tin and iron halides. More specifically, it has been discovered that when heterocyclic amines are mixed with between about 2.8 and 3.2 moles of hydrogen fluoride per mole of amine nitrogen, not only are prior art shortcomings resolved, but an ionic liquid is obtained having desirable salt-like properties, including a low melt temperature. The ionic liquids of the present invention also desirably have a low, water-like viscosity.

Therefore, according to one aspect of the present invention, ionic liquids are provided having melting points below about 100 C, formed by reaction of a heterocyclic amine with between about 2.8 and about 3.2 moles of anhydrous hydrogen fluoride per mole of amine nitrogen.

Ionic liquids according to the present invention may consist of a salt of a single heterocyclic amine according to the present invention, or two or more heterocyclic amines. A single heterocyclic compound may contain a plurality of amine nitrogen atoms, each of which is converted to a salt.

Ionic liquids according to the present invention may be used in known ionic liquid uses, such as preparative chemistry, and also as catalysts. Ionic liquids of the present invention, however, are particularly useful as non-aqueous electrolytes for electrochemical devices such as electrochemical capacitors, photovoltaic devices, potentiometric and voltametric electrochemical sensors, batteries, fuel cells and electrodeposition devices.

Therefore, according to another aspect of the present invention, an electrochemical device is provided having a positive electrode and a negative electrode, both of which are in conductive contact with an ionic liquid according to the present invention as the non-aqueous electrolyte.

Ionic liquids of the present invention are suitable for use in wet etching technologies used in the microelectronic fabrication of semiconductors. In particular the ionic liquids can be used to etch selectively in the presence of aluminum $SiO_2$ layers and structures on silicon wafers and other semiconductor substrates. This etch selectivity can be advantageously used to remove sacrificial silicon oxide coatings on MEMs devices.

Therefore, according to another aspect of the present invention, an anhydrous etching solution for removing silicon oxides is provided in which an effective amount of an ionic liquid according to the present invention is dissolved in at least one anhydrous solvent. For purposes of the present invention silicon oxides are defined as $SiO_2$ and other silicon oxide compounds that may be present.

Any anhydrous solvent in an ionic liquids of the present invention are soluble can be used as the anhydrous solvent. Generally, these are polar anhydrous solvents. Thus, the present invention includes compositions as described above, wherein at least one anhydrous solvent is a polar solvent.

The present invention thus provides a method by which silicon oxide layers may be removed from a semiconductor substrate. Therefore according to yet another aspect of the present invention, a method is provided for removing a silicon oxide layer from a semiconductor substrate in which an anhydrous etching solution according to the present invention is contacted with a silicon oxide layer on the surface of a semiconductor substrate until at least a portion of the silicon oxide is removed. According to one embodiment of this aspect of the invention, the semiconductor substrate is a silicon wafer. According to another embodiment of this aspect of the invention the semiconductor substrate contains at least one aluminum component with a sacrificial oxide coating layer.

Ionic liquids of the present invention, which function as ionic liquids singularly or when two or more are mixed together, are prepared by forming a salt of a heterocyclic amine with hydrogen fluoride. Heterocyclic amines suitable for use with the present invention may be aromatic such as pyrrole, imidazole, purine, pyrazole, pyridine, pyridazine, pyrazine, quinoline, quinazoline, pyrimidine, and the like, or they may be non-aromatic, such as pyrrolidine, pyrrolidone, piperazine, piperidine and the like, which are fully saturated, and pyrroline, and the like, which is non-aromatic, but unsaturated.

Heterocyclic amines suitable for use with the present invention includes single-ring compounds containing from five to seven ring members, with from one to three ring members being a heteroatom, at least one of which is nitrogen. Other suitable heteroatom ring members include oxygen, sulfur, and the like. Single-ring heterocyclic amines containing from one to three nitrogen atoms are preferred, with structures in which all ring heteroatoms are nitrogen atoms being more preferred.

Heterocyclic amines suitable for use with the present invention also include multi-cyclic fused two or three ring structures with from eight to fourteen ring members containing from one to three heteroatoms, at least one of which is nitrogen. Multi-cyclic two ring fused structures containing from eight to ten ring members are preferred. Again, the ring structure may include other heteroatoms such as oxygen, sulfur), and the like. Multi-cyclic fused ring structures containing from one to three nitrogen atoms are preferred, with structures in which all ring heteroatoms are nitrogen being the most preferred.

Heterocyclic amines suitable for use with the present invention include dimers and trimers of the same or different single-ring or multi-cyclic fused-ring structure directly bonded together, such as bis-pyridine. Dimers are preferred. Instead of being directly linked together, the ring structures of dimers and trimers may be linked by appropriate bi-functional ligands.

Heterocyclic amines suitable for use with the present invention may also be ring-substituted. A single ring substituent may be present, or up to three of the same or different substituents may be employed. The ring-substituents may be attached to a carbon atom or a suitable nitrogen atom.

Examples of suitable ring-substituents include, but are not limited to, halogen (including chlorine, bromine, fluorine and iodine), amino, cyano, hydroxyl, nitro, keto, phenyl, one to three carbon atom lower alkyl, two to four carbon atom alkene or alkyne, three to six carbon atom cycloalkyl or cycloalkene, one to four carbon atom aldehyde, $-R_1C(=O)R_2$, $-R_1OR_2$, $-R_1OC(=O)OR_2$, $-R_1C(=O)OR_2$, and the like, wherein $R_1$ is a bond, a one to three carbon atom lower alkyl, a two to three carbon atom alkene, or phenyl, and $R_2$ is hydrogen, a one to three carbon atom lower alkyl, a two to three carbon atom alkene or phenyl. The $R_1$ and $R_2$ lower alkyl, alkene and phenyl groups may be further optionally substituted with one or more halogen, amino, cyano, hydroxyl, nitro, phenyl, one to three carbon atom lower alkyl and one to three carbon atom lower alkoxy. The preferred substituent groups include $C_aH_bBr_cCl_dF_eI_fN_gO_h$, where a is between 1 and 3, b, e are between 0 and 9, c, d, f, g and h are each between 0 and 2, and the sum of b through h is between 1 and 9, inclusive. When more than one substituent group is present, the substituents may be the same or different.

Heterocyclic amine salts according to the present invention have a melting point below about 100 C. For purposes of the present invention, "melting point" is determined by Differential Scanning Calorimetry. Among the heterocyclic amine salts of the present invention, those having a melting point less than about 60 C are preferred, with heterocyclic amine salts having melting points below room temperature being even more preferred. For purposes of the present invention, room temperature is defined as 25 C. The heterocyclic amine salts according to the present invention also have a viscosity between about 1 and about 100,000 centipoise when measured at room temperature using a vibrating reed viscometer. A viscosity less than 10,000 centipoise is preferred.

Ionic liquids according to the present invention have a specific conductivity between about one and about 600 milli-siemens/cm (mS/cm) and preferably greater than about 20 milli-siemens/cm, as measured by a common conductivity meter suitable for measuring conductivity in corrosive atmospheres such as in hydrogen fluoride.

Examples of specific heterocyclic amine compounds within the scope of the present invention include pyridine and substituted pyridine compounds such as α-picoline (2-methyl-pyridine), 2-amino-3-methylpyridine, niacin, niacinamide (Vitamin B), 2-aminopyridine, β-picoline(3-methylpyridine), 3-cyanopyridine, 4-cyanopyridine, 4-dimethylaminopyridine, 1,3-di-(4-pyradyl)-propane, 4-ethylpyridine, γ-picoline (4-methylpyridine), 2,6-lutidine, 3,5-lutidine, mixed picolines, mixed alkyl pyridines, 4-phenylpropylpyridine, polyalkylpyridine, pyridoxine (Vitamin $B_6$), 3-pyridylcarbinol, 2-vinylpyridine, 4-vinylpyridine, and the like.

Examples of non-pyridine heterocyclic amines also suitable for use with the present invention include piperidine and substituted piperidine compounds such as 2-ethanol-piperidine, 1,3-di-(4-piperidinyl)propane, and the like; pyrrole and substituted pyrroles; pyrrolidine and substitutes pyrrolidines; pyrrolidone and substitutes pyrrolidones such as N-methylpyrrolidone; imidazolines and substituted imidazolines; oxazole and substituted oxazoles; thiazole and substituted thiazoles; pyrazole and substituted pyrazoles; pyrroline and substituted pyrrolines; pyrimidine and substituted pyrimidines; purine and substitutes purines; quinoline and isoquinoline and substituted quinolines and isoquinolines; and the like.

Ionic liquids according to the present invention may be prepared simply by mixing together one or more heterocyclic amines with a stoichiometric amount of anhydrous HF, i.e., between about 2.8 and about 3.2 moles of anhydrous HF per mole of amine nitrogen, in a metal or plastic sealed vessel with an agitator, such as an Autoclave, with a sealed connection to the anhydrous HF supply, typically another sealed vessel. The vessel should be jacketed to remove heat inasmuch as the salt formation is highly exothermic. The vessels and the connection therebetween are sealed to protect against environmental exposure to anhydrous HF. The anhydrous HF may also be delivered in the form of Olah's reagent, the preparation of which is disclosed in U.S. Pat. No. 5,073,674.

No additional solvent is generally employed, although it may be advantageous in some circumstances to carry out a reaction in a solvent that is an ionic liquid, in particular, an ionic liquid according to the present invention. Excess reagents are readily removed by distillation because of the negligible vapor pressure of the salt product.

Optional solvents may then be used that are not ionic liquids, and are preferably polar in nature, to dissolve and further dilute the viscosity of the ionic liquids of the present invention, for example for use in electrochemical applications such as fuel cells, electrochemical capacitors, non-aqueous rechargeable batteries such as lithium batteries, photovoltaic cells and the like. Preferred solvents include propylene carbonate, acetonitrile, and the like.

Ionic liquids according to the present invention include mixtures of two or more ionic liquid compounds according to the present invention. Such ionic liquids may be prepared by starting with a corresponding mixture of heterocyclic amines, or each ionic liquid compound may be individually prepared and then combined to form an ionic liquid mixture.

The ionic liquids according to the present invention may be used for a wide range of purposes; for example, the liquids are useful for carrying out applications such as chemical reactions in preparative chemistry where a polar but non-aqueous solvent or a solvent with negligible vapor pressure is required. The ionic liquids according to the present invention may also be employed as thermal storage fluids. They may further be employed as inert media, for example, for dissolving ionic species such as transition metal complexes, and, either alone, or after complexing with other metal ions, as catalysts, or as chemical reagents.

Solvent system applications wherein a polar but non-aqueous solvent is required for which the ionic liquids of the present invention are useful include cellulose recycling, catalytic cracking reactions such as polyethylene recycling, chiral catalysis, coupling reactions, such as the Heck reaction, sulfonation reactions, nitration reactions, oxidation reactions, nucleophilic substitution reactions, olefin polymerization reactions, actinide extractions, alkylation reactions, hydroformylation reactions, dimerization reactions, hydrogenation reactions, Diels-Alder reactions, metathesis reactions, arylation reactions, Friedel-Crafts reactions, and the like.

The ionic liquids of the present invention are particularly well suited as non-aqueous electrolytes in electrochemical devices such as electrochemical capacitors, photovoltaic devices, potentiometric and voltametric electrochemical sensors, batteries, fuel cells and electrodeposition devices. The present invention therefore includes such electrochemical devices in which a positive electrode and a negative electrode are in conductive contact with a non-aqueous electrolyte essentially consisting of an ionic liquid of the present invention. Other conventional electrolyte additives may be present. The devices are otherwise conventional and require no further description. One having ordinary skill in the art will understand how to use ionic liquids according to the present invention as a non-aqueous electrolyte for such devices.

The ionic liquids of the present invention are also particularly well suited for use in etchant compositions for the removal of silicon oxide layers from semiconductor substrates. Etchant compositions are prepared by dissolving an effective amount of one or more ionic liquids according to the present invention in one or more anhydrous solvents. A preferred ionic liquid is pyridine.3HF.

The solvents are preferably polar in nature and include common solvents such as propylene carbonate, acetonitrile, and the like. Preferred anhydrous solvents are chosen from polyols, carboxylic acids, derivatives of carboxylic acids, organic sulfur compounds, and mixtures of two or more thereof.

Among others, examples of polyols include ethylene glycol, propylene glycol, polymethylene glycol, polyethylene glycol and glycerol. In particular polyols with relatively low viscosity are preferred. Further, polyalkylene glycols, in particular polyethylene glycols with a number-average molecular weight of 250 to 6,000 are also preferred, and more preferably have a molecular weight of 250 to under 5,000 and in particular 250 to 1,000.

The carboxylic acids include aliphatic, cycloaliphatic and aromatic acids that are liquid at ambient conditions, and may have one or more acid groups. Among others, examples include formic acid, acetic acid and propionic acid. Acid derivatives of carboxylic acids such as their esters or their amides are also appropriate solvents. It is further possible to use acrylic derivatives the carboxylic acids or the carboxylic acid derivatives. Hydroxyl groups and halogens are included among possible substituents. Amino carboxylic acids are also included among the possible solvents, as well as nitriles such as acetonitrile.

Anhydrous organic sulfur compounds, such as sulfates, sulfonates, sulfoxides, sulfones or sulfites are also appropriate solvents, including DMSO, dimethyl sulfite, diethyl sulfite, glycol sulfite, dimethyl sulfone, diethyl sulfone, dipropyl sulfone, dibutyl sulfone, tetramethylene sulfone, methyl sulfolane, diethyl sulfoxide, dipropyl sulfoxide, dibutyl sulfoxide, tetramethylene sulfoxide, ethyl methane sulfonate, 1,4-butane diolbis(methane sulfonate), diethyl sulfate, dipropyl sulfate, dibutyl sulfate, dihexyl sulfate, dioctyl sulfate, and the like.

Furthermore, ethylene carbonate, propylene carbonate, dimethyl carbonate, diethyl carbonate, dipropyl carbonate, diisopropyl carbonate, dibutyl carbonate are also appropriate anhydrous solvents. Propylene carbonate is particularly preferred.

Aliphatic and aromatic amines, which promote surface-active properties, may also be added to the etching compositions. Aliphatic amines with a chain length of 5 to 12 carbon atoms are preferably used. The amines may be substituted, if necessary for purposes of solubility, wherein OH groups or halogenide residues are possible substituents, among others.

The concentration of the ionic liquid can be adjusted to provide a silicon oxide layer removal rate up to about 1250 Angstroms per minute. It is possible to obtain a rate as low as one Angstrom per minute. These rates are obtained with ionic liquid concentrations between about 0.01 and about 10% by weight and preferably between about 0.1 and about 5 wt %.

Other acids conventionally used in semiconductor etching compositions may be added in art-recognized quantities. Examples of such acids include, but are not limited to, hydrofluoric acid, fluorosulfonic acid, sulfuric acid, nitric acid, acetic acid, orthophosphoric acid, hydrobromic acid, and the like. Other silicon oxide removing compounds can be present, such as ammonium fluoride and other fluoride compounds.

The etching compositions of the present invention are widely applicable to a variety of silicon oxide etching processes that are included within the scope of the present invention. The etching processes are essentially conventional and require no further description, except to note that the absence of water in the etching compositions of the present invention allows for an extremely high selective removal of silicon oxide layers in the presence of aluminum. The etching compositions of the present invention are particularly well suited for, and the etching methods of the present invention include, methods in which sacrificial silicon oxide coating layers are removed from aluminum components of semiconductor substrates, such as the aluminum sensors of Micro-Electronic Mechanical (MEMs) devices.

A few of a number of preferred embodiments of the invention are illustrated in the following non-limiting examples.

EXAMPLES

Example 1

Formation of Pyridine Salt with Hydrogen Fluoride

About 60 grams of anhydrous hydrogen fluoride was added slowly to about 55 grams of pyridine contained in an autoclave with stirring, giving a pyridine to HF mole ratio of 1:3.

When the heat of the reaction subsided and the mixture cooled down, the autoclave contained 115 grams of a liquid, boiling at 180 C, 90 C higher than that of pyridine and 160 C higher than that of hydrogen fluoride. The liquid could not be separated into the constituents. The analysis of the material confirmed the structure of the new compound as the ionic liquid [pyridine.H$^+$] [H$_2$F$_3$]$^-$ (or pyridine.3HF). The conductivity of the pure ionic liquid was measured as 98 mS/cm. The liquid did not etch borosilicate glass, unlike Olah's reagent, which reacts with glass.

The ionic liquid was dissolved in propylene carbonate, where it was soluble in all proportions, and the conductivity was measured. The conductivity smoothly varied from 0 to 98 mS/cm as a function of the ionic liquid concentration.

The ionic liquid of was also dissolved in acetonitrile, where it again was soluble in all proportions, and the conductivity measured. The conductivity smoothly varied again, with a maximum at 104 mS/cm at about 80 wt % ionic liquid concentration.

Example 2

Formation of α-Picoline Salt with Hydrogen Fluoride

About 60 grams of anhydrous hydrogen fluoride was added slowly to about 69 grams of α-picoline contained in an autoclave with stirring, giving a picoline to HF mole ratio of 1:3. When the heat of the reaction subsided and the mixture cooled down, the autoclave contained 129 grams of a liquid, boiling at 200 C, 80 C higher than α-picoline and 180 C higher than hydrogen fluoride. The liquid could not be separated into the constituents. The analysis of the material confirmed the structure of the new compound as the ionic liquid [α-picoline.H$^+$] [H$_2$F$_3$]$^-$ (or α-picoline.3HF). The conductivity of the pure ionic liquid was measured as 73 mS/cm. The liquid did not etch borosilicate glass, unlike Olah's reagent, which reacts with glass.

Example 3

Silicon Dioxide Etching

Solutions of the pyridine salt of Example 1 were dissolved in propylene carbonate at varying concentrations. Silicon dioxide coated silicon wafers, used for MEMS device manufacture, were dipped in it. The etching rate was very fast, with rates being proportional to the pyridine salt concentration in the propylene carbonate.

The foregoing examples illustrate a wide variety of compounds according to the present invention that may be prepared having utility in a wide variety of solvent applications, and as non-aqueous electrolytes for various electrochemical devices. It will be apparent to one of skill in the art based on the properties apparent from the foregoing examples that a wide range of other applications are possible with the compounds according to the invention, and that the invention includes a wide range of compounds that are not specifically demonstrated by the examples, but that may be obtained by application of the principles demonstrated.

What is claimed:

1. An ionic liquid comprising a salt of at least one heterocyclic amine and between about 2.8 and about 3.2 moles of anhydrous hydrogen fluoride per mole of amine nitrogen, the ionic liquid having a melting point less than about 100 C and having a specific conductivity greater than about 20 millisiemens/cm, wherein said heterocyclic amine is selected from the group consisting of substituted and unsubstituted pyrroles, substituted and unsubstituted pyrazoles, substituted and unsubstituted pyridines, substituted and unsubstituted pyrazines, substituted and unsubstituted pyrimidines, substituted and unsubstituted pyridazines, substituted and unsubstituted thiazoles, substituted and unsubstituted oxazoles, substituted and unsubstituted triazoles, substituted and unsubstituted pyrrolidines, substituted and unsubstituted pyrrolidones, substituted and unsubstituted piperazines, substituted and unsubstituted piperidines and substituted and unsubstituted pyrrolines.

2. The ionic liquid of claim 1, having a melting point less than about 60 C.

3. The ionic liquid of claim 2, having a melting point less than about 25 C.

4. The ionic liquid according to claim 1, consisting of one heterocyclic amine ionic compound.

5. The ionic liquid according to claim 1, consisting of two or more heterocyclic amine ionic compounds.

6. The ionic liquid of claim 1, wherein said heterocyclic amine is a pyridine or a picoline.

7. An ionic liquid comprising a salt of at least one heterocyclic amine and between about 2.8 and about 3.2 moles of anhydrous hydrogen fluoride per mole of amine nitrogen, the ionic liquid having a melting point less than, about 10° C. and having a specific conductivity greater than about 20 millisiemens/cm, wherein said heterocyclic amine, is a multicyclic fused ring structure containing from 8 to 14 ring members, with from 1 to 3 ring members being a heteroatom selected from the group consisting of nitrogen, oxygen and sulfur, wherein at least one of said heteroatoms is nitrogen.

8. The ionic liquid of claim 7, wherein said heterocyclic amine is selected from the group consisting of substituted and unsubstituted quinolines, substituted and unsubstituted quinoxalines, substituted and unsubstituted purines and substituted and unsubstituted isoquinolines.

9. An anhydrous etching solution for removing silicon oxides comprising an effective amount of an ionic liquid dissolved in at least one anhydrous solvent, the ionic liquid comprising a salt of at least one heterocyclic amine and between about 2.8 and about 3.2 moles of anhydrous hydrogen fluoride per mole of amine nitrogen, the ionic liquid having a melting point less than about 100 C;

wherein said heterocyclic amine is selected from the group consisting of substituted and unsubstituted pyrroles, substituted and unsubstituted pyrazoles, substituted and unsubstituted pyridines, substituted and unsubstituted pyrazines, substituted and unsubstituted, substituted and unsubstituted pyridazines, substituted and unsubstituted thiazoles, substituted and unsubstituted oxazoles, substituted and unsubstituted triazoles, substituted and unsubstituted pyrrolidines, substituted and unsubstituted pyrrolidones, substituted and unsubstituted piperazines, substituted and unsubstituted piperidines and substituted and unsubstituted pyrrolines.

10. The anhydrous etching solution of claim 9, wherein said ionic liquid is present in an amount effective to remove a silicon oxide layer at a rate up to about 1250 Angstroms per minute.

11. The anhydrous etching solution of claim 9, comprising pyridine 3HF in propylene carbonate.

12. A method for removing a silicon oxide layer from a semiconductor substrate comprising contacting the anhydrous etching solution of claim 9 with a silicon oxide layer on the surface of a semiconductor substrate until at least a portion of the silicon oxide layer is removed.

13. The method of claim 12, wherein said semiconductor substrate comprises an aluminum component having a sacrificial silicon oxide coating layer.

* * * * *